US00PP28165P2

(12) United States Plant Patent
Randag

(10) Patent No.: US PP28,165 P2
(45) Date of Patent: Jul. 4, 2017

(54) VARIETY OF CALLA LILY PLANT NAMED 'HALIFAX'

(50) Latin Name: *Zantedeschia sprengeri*
Varietal Denomination: Halifax

(71) Applicant: Sande B.V., 't Zand (NL)

(72) Inventor: Cecilius Jan-Jochem Randag, 't Zand (NL)

(73) Assignee: Sande B.V., 't Zand (NL)

( * ) Notice: Subject to any disclaimer, the term of this patent is extended or adjusted under 35 U.S.C. 154(b) by 0 days.

(21) Appl. No.: 14/757,336

(22) Filed: Dec. 17, 2015

(51) Int. Cl.
*A01H 5/02* (2006.01)

(52) U.S. Cl.
USPC ..... Plt./490

(58) Field of Classification Search
USPC ..... Plt./490
CPC ..... A01H 5/0272
See application file for complete search history.

*Primary Examiner* — Kent L Bell
(74) *Attorney, Agent, or Firm* — The Webb Law Firm

(57) ABSTRACT

'Halifax' is a new variety of calla lily plant having inflorescences with a white/purple-colored spathe that produces 3-10 inflorescences per tuber. The height of the top of an inflorescence above the soil can reach up to 47 cm, and the leaves are dark green with whitish spots and have a leathery texture.

2 Drawing Sheets

Botanical classification: *Zantedeschia sprengeri*.
Varietal denomination: 'HALIFAX'.

BACKGROUND OF THE NEW PLANT

The present invention comprises a new and distinct cultivar of calla lily, botanically known as *Zantedeschia sprengeri* and hereinafter referred to by the cultivar name 'Halifax'.

'Halifax' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of a *Zantedeschia sprengeri* selection referred to as C03001 (female parent, unpatented) with a *Zantedeschia sprengeri* selection referred to as E439 (male parent, unpatented). 'Halifax' was selected in 2010 by the inventor in 't Zand, The Netherlands as one flowering plant within the progeny of the stated cross.

The first act of asexual reproduction of 'Halifax' by tissue culture was performed by the inventor in September of 2012 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown in 14 cm pots in 't Zand, The Netherlands under greenhouse conditions, which approximate those generally used in horticultural practice. Color references are made to The R.H.S. Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Halifax' which, in combination, distinguish this calla lily as a new and distinct cultivar:

1. Spathe with white color present at the start of flowering on the inner surface from between White Group RHS 155A and 155B that changes to between Purple Group RHS N79A and N79B during senescence;
2. Purple leaf margin; and
3. Colored flower bud.

Further, when compared to calla lily plant named 'Picasso' (U.S. Plant Pat. No. 15,282), 'Picasso' has an upper surface base spathe color of Green-Yellow Group RHS 1D and a second color that varies between Purple Group RHS 76A and Red-Purple Group RHS 74B, whereas 'Halifax' has an upper surface spathe color that varies between Purple Group RHS N79A and N79B, with a second color between White Group RHS 155A and 155B.

Table 1 provides similarities and differences of 'Halifax' to its parents, *Zantedeschia sprengeri* selections C03001 and E439.

TABLE 1

| 'Halifax' | Similarities | Differences |
|---|---|---|
| C03001 | Maculation intensity | Spathe color |
| | Leaf color | Spathe size |
| | Number of inflorescences | Spathe shape |
| E439 | Leaf shape | Spathe color |
| | Plant shape | Number of inflorescences |
| | Purple leaf margin | |

BRIEF DESCRIPTION OF THE DRAWINGS

The accompanying photographic drawings illustrate the new variety, with the colors being as nearly true as is possible with color illustrations of this type.

DESCRIPTION OF THE NEW PLANT

The Plant

Figure 1:
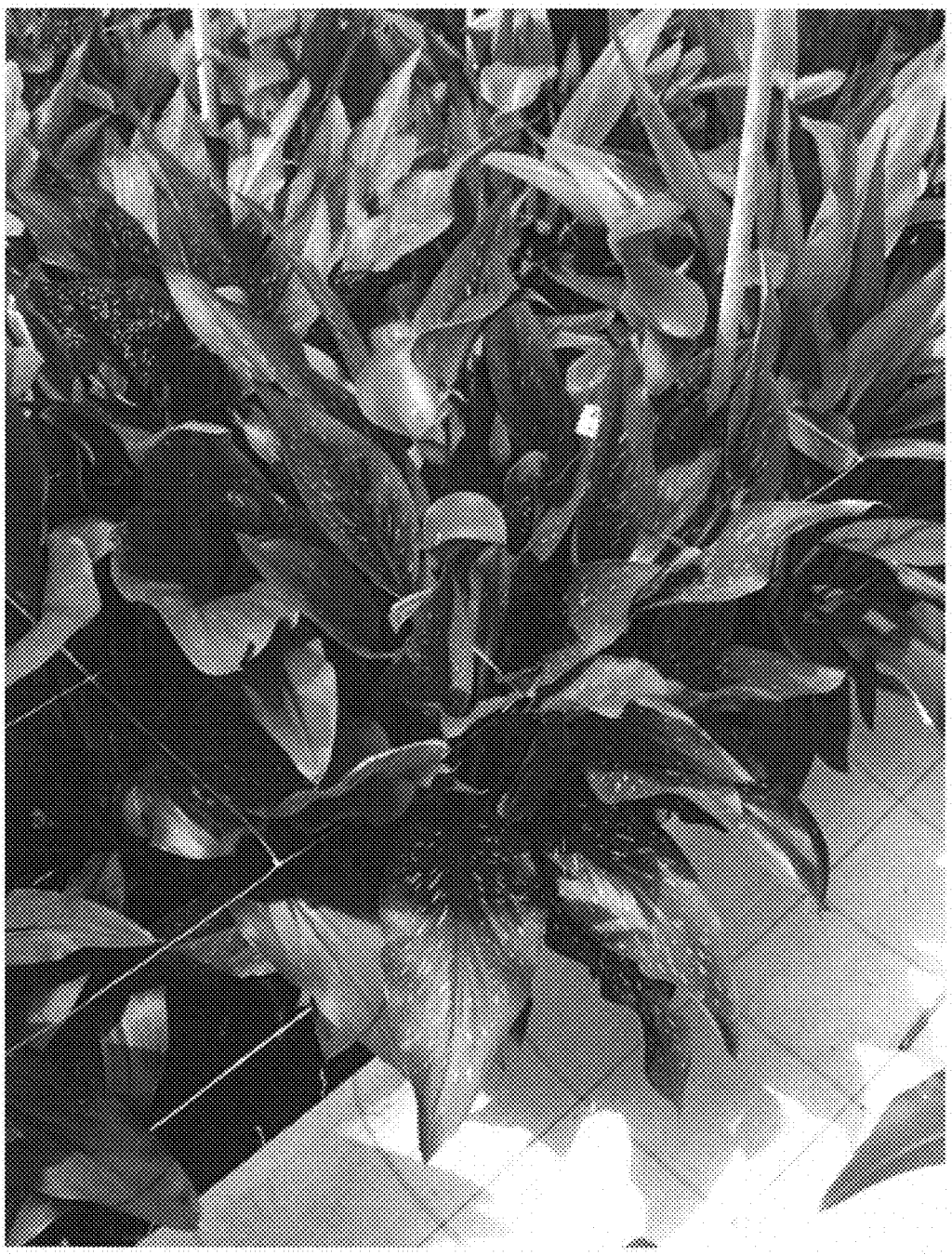
FIG. 1 is a photograph of a plant of the new variety.
Figure 2:
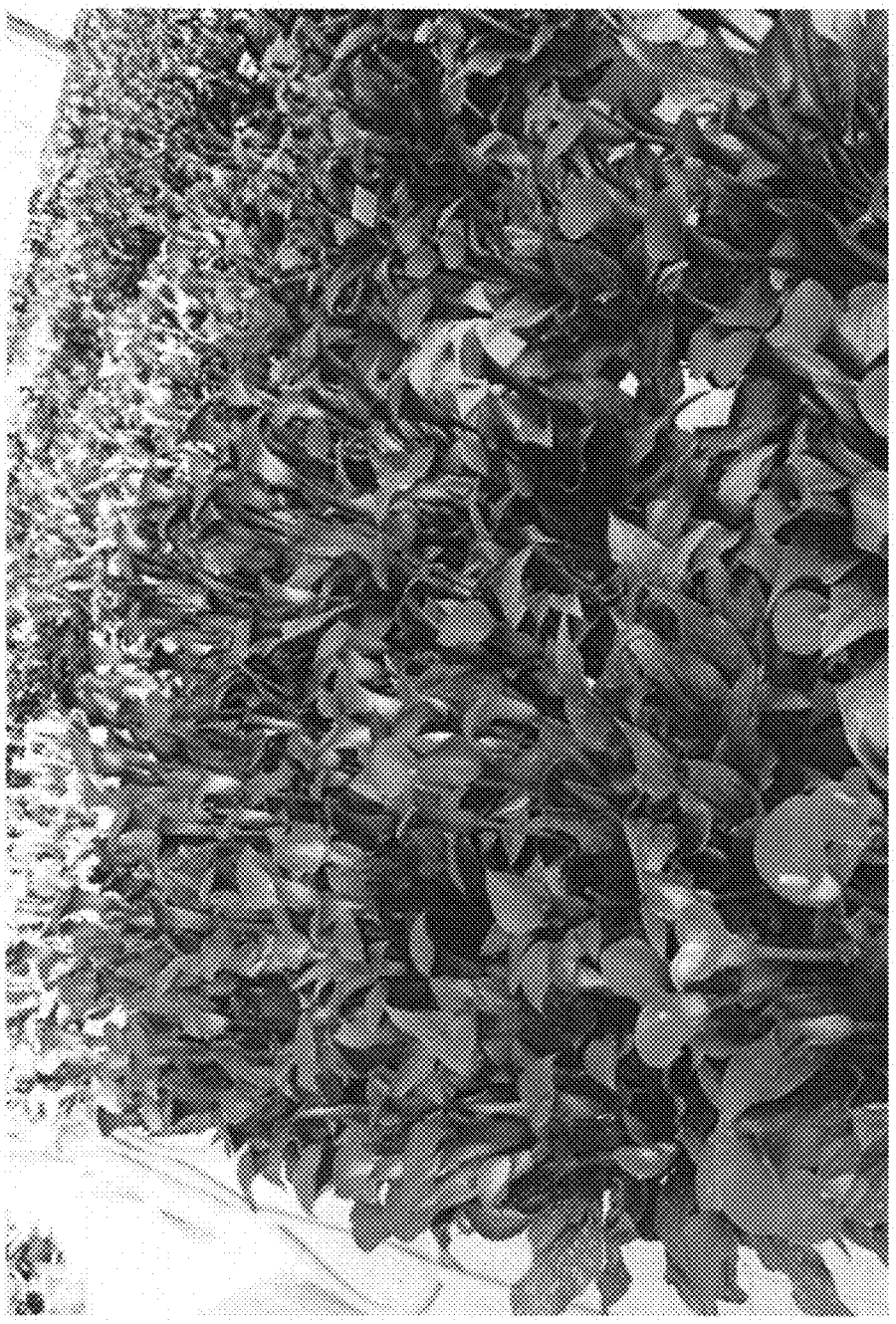
FIG. 2 is a photograph of a group of multiple plants of the new variety.

Size:

*Height of the leaf canopy above the soil.*—16.5-46.5 cm.

*Height of top of inflorescence above the soil.*—23-47 cm.

*Diameter.*—7-43 cm.

Form: Erect.

Number of inflorescences per tuber:

*Size* 14-16 *cm in diameter.*—3-6 inflorescences.

*Size* 16-18 *cm in diameter.*—4-8 inflorescences.

*Size* 18-20 *cm in diameter.*—6-10 inflorescences.

Branches:

*Character.*—Many; like the variety 'Odessa' (U.S. Plant Pat. No. 18,833).

*Color.*—Between Yellow-Green Group RHS 147B and Greyed-Purple Group RHS 187B.

Leaves:

*Size.*—Width: 3-12 cm. Length: 12.5-21.5 cm.

*Number per plant.*—14-26.

*Shape.*—Lanceolate.

*Color.*—Upper surface: Green Group RHS 137A to Yellow-Green Group RHS 147A. Lower surface: Yellow-Green Group RHS 147A.

*Margin.*—Undulate; having a color of Greyed-Purple Group RHS 184A and 184B.

*Veins.*—Configuration: Pinnate. Color: Green Group RHS 137A to 137C.

*Surface quality.*—Leathery.

*Petiole.*—Length: 8.5-25 cm. Color: The base is White Group RHS 155A, and the upper part is between Greyed-Red Group RHS 178A and Greyed-Purple Group RHS 187A.

Roots:

*Color.*—White.

*Branching.*—Similar to other *Zantedeschia* varieties.

The Inflorescence and Seeds

Spathe:

*Size.*—Length (measured from opening to tip): 5.5-11 cm. Width: 3-7 cm. Height: 6-11 cm.

*Color.*—Upper surface: Varies between Purple Group RHS N79A and N79B, with a second color between White Group RHS 155A and 155B. Lower surface: Varies between Red-Purple Group RHS 59B and 59C.

*Vein color.*—Between Red-Purple Group RHS 59A and Greyed-Purple Group RHS 187C.

*Shape.*—Cupped.

Spadix:

*Size.*—Length: 25-30 mm. Diameter: 4-7 mm.

*Color.*—Between Yellow Group RHS 12A and 12B.

*Position relative to spathe.*—Upright.

Peduncle:

*Size.*—Length: 15.5-39 cm. Diameter: 6-10 mm.

*Color.*—The upper part is between Red-Purple Group RHS 59A and 59B, and the lower part is Green-White Group RHS 157C.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: More than 20. Pollen amount: Similar to 'Picasso' (U.S. Plant Pat. No 15,282). Color: Between White Group RHS 155A and 155B.

*Anther.*—Shape: Round. Length: Less than 1 mm. Color: Between Yellow Group RHS 12A and 12B.

*Filament.*—Length: Less than 1 mm. Color: Between White Group RHS 155A and 155B.

*Pistils.*—Number: 15 to 30. Length beyond perianth: About 1 mm.

*Stigma.*—Shape: Round. Size: Less than 1 mm.

*Style.*—Length: Less than 1 mm. Color: Between Greyed-Purple Group RHS 186A and 186B.

*Ovaries.*—Texture: Smooth. Length: Between 1 to 10 mm. Width: Between 1 to 10 mm. Color: Top color is between Yellow Group RHS 12A and 12B, bottom color is from White Group RHS 155B to Green-White Group RHS 157C.

Seeds:

*Length.*—4-7 mm.

*Width.*—3-6 mm.

*Color.*—Between Yellow-Green Group RHS 150A and 151A.

*Amount.*—Between 1-60.

General

Disease resistance: No unusual susceptibility to diseases noticed to date.

Pest resistance: No unusual susceptibility to pests noticed to date.

Heat tolerance: No heat tolerance.

Hardiness: Not hardy.

Flowering: Tubers planted in a greenhouse in The Netherlands in February produce inflorescences in April. Tubers planted outdoors in The Netherlands in May produce inflorescences in July.

Lastingness: About two weeks on the plant.

Fragrance: None.

I claim:

1. A new and distinct variety of calla lily plant named 'Halifax' as herein described and illustrated.

* * * * *